(12) United States Patent
Pompilio, III et al.

(10) Patent No.: US 10,594,636 B1
(45) Date of Patent: Mar. 17, 2020

(54) ELECTRONIC MESSAGE NORMALIZATION, AGGREGATION, AND DISTRIBUTION

(71) Applicant: SimpleC, LLC, Atlanta, GA (US)

(72) Inventors: Daniel V. Pompilio, III, Smyrna, GA (US); Jason Zamer, Atlanta, GA (US); Chantal Kerssens, Atlanta, GA (US); Tim Sebel, Atlanta, GA (US); Douglas V. Nelson, Jr., Atlanta, GA (US)

(73) Assignee: SimpleC, LLC, Atlanta, GA (US)

( * ) Notice: Subject to any disclaimer, the term of this patent is extended or adjusted under 35 U.S.C. 154(b) by 805 days.

(21) Appl. No.: 14/540,697

(22) Filed: Nov. 13, 2014

Related U.S. Application Data

(63) Continuation-in-part of application No. 14/467,845, filed on Aug. 25, 2014, now abandoned, which is a continuation-in-part of application No. 13/447,877, filed on Apr. 16, 2012, now Pat. No. 8,814,359, which is a continuation-in-part of application No. 13/330,779, filed on Dec. 20, 2011, which is a continuation of application No. 12/243,404, filed on Oct. 1, 2008, now Pat. No. 8,096,657.

(60) Provisional application No. 61/475,285, filed on Apr. 14, 2011, provisional application No. 60/997,168, filed on Oct. 1, 2007.

(51) Int. Cl.
*A61B 5/16* (2006.01)
*H04L 12/58* (2006.01)

(52) U.S. Cl.
CPC .............. *H04L 51/066* (2013.01); *A61B 5/16* (2013.01); *H04L 51/10* (2013.01)

(58) Field of Classification Search
None
See application file for complete search history.

(56) References Cited

U.S. PATENT DOCUMENTS

| | | | |
|---|---|---|---|
| 5,657,256 A | 8/1997 | Swanson et al. | |
| 6,430,174 B1 | 8/2002 | Jennings et al. | |
| 8,814,359 B1 | 8/2014 | Pompilio, III et al. | |
| 2002/0049852 A1* | 4/2002 | Lee | H04L 29/06 709/231 |
| 2002/0059339 A1* | 5/2002 | McCormick | G06F 17/3089 715/202 |
| 2002/0169635 A1* | 11/2002 | Shillingburg | G06F 19/3462 705/2 |
| 2003/0046401 A1* | 3/2003 | Abbott | G06F 9/4443 709/228 |
| 2006/0294108 A1* | 12/2006 | Adelson | G06Q 10/06 |
| 2008/0162352 A1* | 7/2008 | Gizewski | G06F 19/3456 705/50 |

(Continued)

*Primary Examiner* — Bruk A Gebremichael
(74) *Attorney, Agent, or Firm* — Jones Day

(57) ABSTRACT

A system that provides an interface layer through which communications to users can be normalized by making consistent the value-reads (e.g., format) of the communications. The information or message inputted into the system can be used in each aspect of the system to personalize the user's experience. Also, when the system receives information/signals from the user himself/herself (e.g., time it takes to read or transmit a message, choice of communication, etc.), the system can adapt the user's experience to the user's cognitive wellness. The system includes normalization of messages for message aggregation and message distribution.

5 Claims, 3 Drawing Sheets

(56) References Cited

U.S. PATENT DOCUMENTS

| | | | |
|---|---|---|---|
| 2009/0106645 A1* | 4/2009 | Knobel | G06F 17/30056 715/236 |
| 2009/0198777 A1* | 8/2009 | LaFreniere | H04L 12/5875 709/206 |
| 2009/0313582 A1* | 12/2009 | Rupsingh | G06F 3/04817 715/835 |
| 2009/0323905 A1* | 12/2009 | Fields | H04M 1/72597 379/52 |
| 2011/0194629 A1* | 8/2011 | Bekanich | H04M 3/42382 375/259 |
| 2012/0149404 A1* | 6/2012 | Beattie, Jr. | H04M 1/274508 455/466 |

* cited by examiner

ELECTRONIC MESSAGE NORMALIZATION, AGGREGATION, AND DISTRIBUTION

CROSS-REFERENCE TO RELATED APPLICATIONS

This application is a continuation-in-part of and claims priority to co-pending U.S. patent application Ser. No. 14/467,845, entitled "Memory Recollection Training System and Method of Use Thereof", filed Aug. 25, 2014, which is a continuation-in-part of and claims priority to U.S. patent application Ser. No. 13/447,877, now U.S. Pat. No. 8,814,359, entitled "Memory Recollection Training System and Method of Use Thereof", filed Apr. 16, 2012, which claims priority to U.S. Provisional Application No. 61/475,285, entitled "Memory Recollection Training System", filed on Apr. 14, 2011, all of which are incorporated herein by reference in their entireties. U.S. Pat. No. 8,814,359 also is a continuation-in-part of and claims priority to U.S. patent application Ser. No. 13/330,779, entitled "Systems and Methods for Aiding Computing Users Having Sub-Optimal Ability", filed on Dec. 20, 2011, which is a continuation of and claims priority to U.S. patent application Ser. No. 12/243,404, now U.S. Pat. No. 8,096,657, entitled "Systems and Methods for Aiding Computing Users Having Sub-Optimal Ability", filed on Oct. 1, 2008, which claims priority to U.S. Provisional Patent Application No. 60/997,168, filed on Oct. 1, 2007, entitled "Systems and Methods for Instruction and Aid of Aging Computer Users", all of which are incorporated herein by reference in their entireties.

BACKGROUND OF THE INVENTION

1. Field of the Invention

This invention relates, generally, to computer-implemented socialization tools. More particularly, it relates to a communication tool and use thereof for social benefit in a variety of users, for example sufferers of dementia.

2. Description of the Prior Art

Cognitive wellness in all human beings is affected by a plethora of internal and external factors, including age, intelligence, culture, stress levels, anxiety, nutrition, and medication, among others. In turn, cognitive wellness itself can affect social capacities, performance on various tests, and basic abilities to function on a daily basis, among others. Therefore, persons with lower cognitive wellness might have lower test scores or difficulties performing basic tasks.

These difficulties are further exacerbated in individuals having diminished or declining physical (i.e., neurophysiological) or mental (i.e., cognitive or logic) capacities. Individuals prone to these diminished or declining physical or mental capacities can include the elderly, mentally handicapped individuals, and those who have suffered debilitating injury or disease. These individuals are particularly prone to depression and anxiety brought on by feelings of helplessness and isolation caused by a decline in physical or mental capacities.

For example, in elderly persons with dementia, conventional memory aids and drugs are used for treatment. Various memory aids are known but are not sufficiently personalized to each person to provide that person with daily relief and comfort in social settings. Drugs, such as cholinesterase inhibitors, used in treatment of dementia, merely treat the symptoms rather than the underlying root of the symptoms and cannot be the sole treatment method of dementia. Moreover, drugs are invasive and tend to have enhanced side effects in the elderly. These side effects, including chemical imbalances in the body, can hinder a patient's independence and comfort in contacting his/her social network (i.e., due to memory problems, agitation, nausea, etc.), thereby also enhancing feelings of hopelessness.

The lack of treatment and effective memory aids lead to individuals having lower cognitive capabilities feeling isolated and incapable of communicating with others, including caretakers, family, and friends. Adding to this is that there is a wide variety of communication tools (e.g., email, social media, etc.) that cannot all be remembered or accessed by these individuals. Further, individuals with lower cognitive abilities may have difficulties checking the news because of the large number of news sources available, leading to further feelings of isolation. This is true even with individuals with higher cognitive abilities, as there is no effective manner of having a unified user interface for transmitting and receiving messages to and from a multitude of sources.

Accordingly, what is needed is an improved system and method for communication between or among individuals and sources. However, in view of the art considered as a whole at the time the present invention was made, it was not obvious to those of ordinary skill how the art could be advanced.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

SUMMARY OF THE INVENTION

The long-standing but heretofore unfulfilled need for a unified, normalized interface for communication is now met by a new, useful and nonobvious invention.

In an embodiment, the current invention is a computer-implemented, a computer-based system, and/or a tangible non-transitory computer readable-medium having computer executable instructions, when executed by a processor, for performing a method of running a software program on a computing device, the computing device operating under an operating system, the method including issuing instructions from the software program. A primary method of communication is received for each of a plurality of contacts, where the primary method of communication is associated with a set of allowable message parameters. A request is received to transmit/send a message to a recipient from the plurality of contacts. It is determined whether the message meets the allowable message parameters for the primary method of communication for the recipient. The message is sent via the primary method of communication if the message conforms to the allowable message parameters of the primary method of communication. If the message does not conform to the allowable message parameters of the primary method of communication, then the message is sent via a secondary method of communication, where the secondary method of communication would have its own allowable message parameters that conform to the message.

The plurality of contacts of an individual may be defined by administering a series of baseline cognitive tests and memory training, such that a test algorithm uses the results of the tests and training to personalize a display of the contacts to the individual.

The secondary method of communication may be preselected by each contact.

In a separate embodiment, the current invention is a computer-implemented, a computer-based system, and/or a tangible non-transitory computer readable-medium having computer executable instructions, when executed by a processor, for performing a method of running a software program on a computing device, the computing device operating under an operating system, the method including issuing instructions from the software program. A message is received from an external source, where the message includes content in a format provided by the external source. An internal destination of the message is determined, where the internal destination includes parameters for receiving the message. A rule database is accessed, and a first set of rules are loaded therefrom, where the rules are application to the parameters associated with the internal destination. The rules are evaluated, and the content of the message is accordingly automatically formatted in order to comply with the parameters. A formatted message is automatically generated, where the message complies with the parameters associated with the internal destination. A second set of rules directed toward a visual display of the formatted message can then be loaded. In accordance with these display rules, the formatted message can be displayed on a display device associated with the internal destination.

The first set of rules may be dynamic and capable of being altered in real-time in accordance with changes to the parameters or to needs of the internal destination.

The first set of rules may include a primary method of communication for the internal destination, where the primary method of communication is associated with a set of allowable message parameters. In this case, it is determined whether the message meets the allowable message parameters for the primary method of communication for the recipient. The message is sent via the primary method of communication if the message conforms to the allowable message parameters of the primary method of communication. If the message does not conform to the allowable message parameters of the primary method of communication, then the message is sent via a secondary method of communication, where the secondary method of communication would have its own allowable message parameters that conform to the message.

The first set of rules may consider (for incorporation into the rules) the content (e.g., text, image, video, etc.) of the message when formatting the message to comply with the parameters.

The first or second set of rules may consider (for incorporation into the rules) the external source of the message, the internal destination of the message, and the content of the message when formatting the message to comply with the parameters.

The internal destination may be an individual end-user. Further, the first or second set of rules can consider a social directory of the individual end-user when formatting the message to comply with the parameters. Alternatively, the first or second set of rules can consider a cognitive ability of the individual end-user when formatting the message to comply with the parameters. In this particular case, the cognitive ability of the individual end-user can be determined by cognitive testing of the individual end-user.

The content of the message may include video content that is normalized to a universal video format in order to comply with the parameters. Similarly, the content of the message may include sound content that is normalized to a universal sound format in order to comply with the parameters.

In a separate embodiment, the current invention is a computer-implemented, a computer-based system, and/or a tangible non-transitory computer readable-medium having computer executable instructions, when executed by a processor, for performing a method of running a software program on a computing device, the computing device operating under an operating system, the method including issuing instructions from the software program. A message is received from an internal source, where the message includes content in a format provided by the internal source. An external destination of the message is determined, where the external destination includes parameters for receiving the message. A rule database is accessed, and a first set of rules are loaded therefrom, where the rules are application to the parameters associated with the internal destination. The rules are evaluated, and the content of the message is accordingly automatically formatted in order to comply with the parameters. A formatted message is automatically generated, where the message complies with the parameters associated with the external destination. A second set of rules directed toward a communication method of the formatted message can then be loaded. In accordance with these communication rules, the formatted message can be transmitted to the external destination.

The first set of rules may be dynamic and capable of being altered in real-time in accordance with changes to the parameters or to needs of the external destination.

The first set of rules may include a primary method of communication for the external destination, where the primary method of communication is associated with a set of allowable message parameters. In this case, it is determined whether the message meets the allowable message parameters for the primary method of communication for the external destination. The message is sent via the primary method of communication if the message conforms to the allowable message parameters of the primary method of communication. If the message does not conform to the allowable message parameters of the primary method of communication, then the message is sent via a secondary method of communication, where the secondary method of communication would have its own allowable message parameters that conform to the message.

The first set of rules may consider (for incorporation into the rules) the content (e.g., text, image, video, etc.) of the message when formatting the message to comply with the parameters.

The first or second set of rules may consider (for incorporation into the rules) the internal source of the message, the external destination of the message, and the content of the message when formatting the message to comply with the parameters.

The internal source may be an individual end-user. Further, the first or second set of rules can consider a social directory of the individual end-user when formatting the message to comply with the parameters. Alternatively, the first or second set of rules can consider a cognitive ability of the individual end-user when formatting the message to comply with the parameters. In this particular case, the cognitive ability of the individual end-user can be determined by cognitive testing of the individual end-user.

The content of the message may include video content that is normalized to a universal video format in order to comply with the parameters. Similarly, the content of the message may include sound content that is normalized to a universal sound format in order to comply with the parameters.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the nature and objects of the invention, reference should be made to the following detailed disclosure, taken in connection with the accompanying drawings, in which.

DETAILED DESCRIPTION OF THE PREFERRED EMBODIMENT

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

In certain embodiment, the message transmission and communication system is an apparatus and a method of increasing or maintaining users' cognitive wellness while providing social benefits to users as well. It is a system that can be used by a variety of users with wide ranges of cognitive abilities. In one embodiment, an individual with normal or advanced cognitive capabilities can use it as an easier mode of communication. In another embodiment, an elderly person with diminished mental capacity may use it to cope with daily life.

The system gathers and organizes sets of information inputted by authorized parties. The information can then be used in a variety of ways and forms, including message transmission. Additionally, the system may provide a medium of communication. If an individual inputs a message, the system can transmit this message to a recipient in a normalized, easy-to-read/display format that is preselected by the user, recipient, or authorized third party. This allows users to communicate with each other more easily.

The system may provide an interface layer through which communications to users can be normalized by making consistent the value-reads (e.g., format) of the communications. The information or message inputted into the system can be used in each aspect of the system to personalize the user's experience. Also, when the system receives information/signals from the user himself/herself (e.g., time it takes to read or transmit a message, choice of communication, etc.), the system can adapt the user's experience to the user's cognitive wellness.

Figure 1:
FIG. 1 depicts an example of the process by which a message may be received or sent through a memory recollection training system.

As depicted in FIG. 1, the system can store an Address Book of the user. The Address Book contains one or more values from a set of information (e.g., name, photo, relationship, contact information, etc.) previously inputted into the system by the user, user's family, authorized third parties, etc. In the user's Mailbox, the user can view a message sent by contacts in the user's Address Book without specifically having to access the user's email system, text messages, social networking websites, etc., similar to the universal inbox disclosed in U.S. Pat. No. 6,430,174 to Jennings, which is incorporated herein by reference in its entirety. A message may include text, images, videos, voice, and/or other method of text-, audio-, video-, or image-based communication. The source of the message is transparent to the user. Messages from the user's social network can appear chronologically to the user automatically in a normalized format, so the user does not feel confusion or anxiety having to take extra steps to view and respond to messages. The term "normalized format" is used herein to refer to a uniform presentation display for the user. Therefore, whereas conventional universal inboxes simply gather messages in one location (i.e., the messages still appear in different formats), in the current invention messages from a plurality of different sources can appear in one standard format.

Additionally, if the user wishes to send a message to a contact in the user's Address Book, the user does not need to choose a method of sending the message. Rather, contacts in the user's social network can have preselected a contact method preference when their set of information was inputted. Therefore, when the user wishes to send a message to a contact, the user simply has to choose to send a message to the contact. The message is composed and sent automatically in the primary method that the contact preselected. If the user's message does not conform to the contact method preference, for example the message being over 140 characters if the contact method preference is TWITTER, then the system can automatically choose the best method of sending the message based on format and/or content or a secondary method preselected by the recipient. Alternatively, in another example, if the primary method of communication is a phone call or voice message and the user begins typing on a computer, the system can automatically choose the best text-based method of transmitting the message.

Optionally, the system can utilize the user's results from baseline testing and memory/cognitive training to define and personalize the content or display of the user's contacts to the user (see U.S. Pat. No. 8,814,359, which is incorporated herein by reference in its entirety). For example, if a user has consistently identified a contact correctly based on the contact's photo, as seen in the baseline testing and training, then the system can automatically reinforce the contact in the Address Book by displaying the contact's photo only when sending or receiving a message.

Example 1—Preferred/Primary Communication Parameters and Channels

In an embodiment, the current invention is a computer-implemented method of sending a text-based, image-based, video-based or audio-based message. An authorized party submits a preferred or primary method of communication for each of a plurality of contacts in a user's address book or directory. The primary method of communication has a first set of allowable message parameters. The user can compose a message by first selecting a recipient from the plurality of contacts. Upon composing the message, it is determined whether the message meets the first set of allowable message parameters. If it meets the parameters or can be formatted to meet the parameters, the message is sent via the primary method of communication. If the message does not meet the parameters and/or cannot be formatted to meet the parameters, the message is sent via a secondary method of communication that has a second set of allowable message parameters to which the message can conform or be formatted to conform. The primary method of communication may be any mode of communication, for example including, but not limited to, email, text message, social network post, social information message, video message, voice message or instant message. The plurality of contacts of a user may be defined by administering a series of baseline cognitive tests and memory training (see U.S. Pat. No. 8,814,359). A test algorithm can utilize the results of the baseline tests and memory training to personalize the display or content of the plurality of contacts for the user.

Example 2—Message Aggregation/Receipt

In an embodiment, the current system is a communication interface that automatically chooses and formats how to present and process a message or response based on the preselected communication method and/or based on the transaction method. The in-basket presents the message (e.g., email, text, tweet, text document, etc.) to the recipient/user in the same form (look and feel) with no differentiation or identification of the original communication product/method. When the user responds to the normalized message, the response can be transmitted through the system to the sent-from address in the same original communication product/method (tweet, text, email, etc.) as used by the original sender, as managed by the system.

Figure 2:
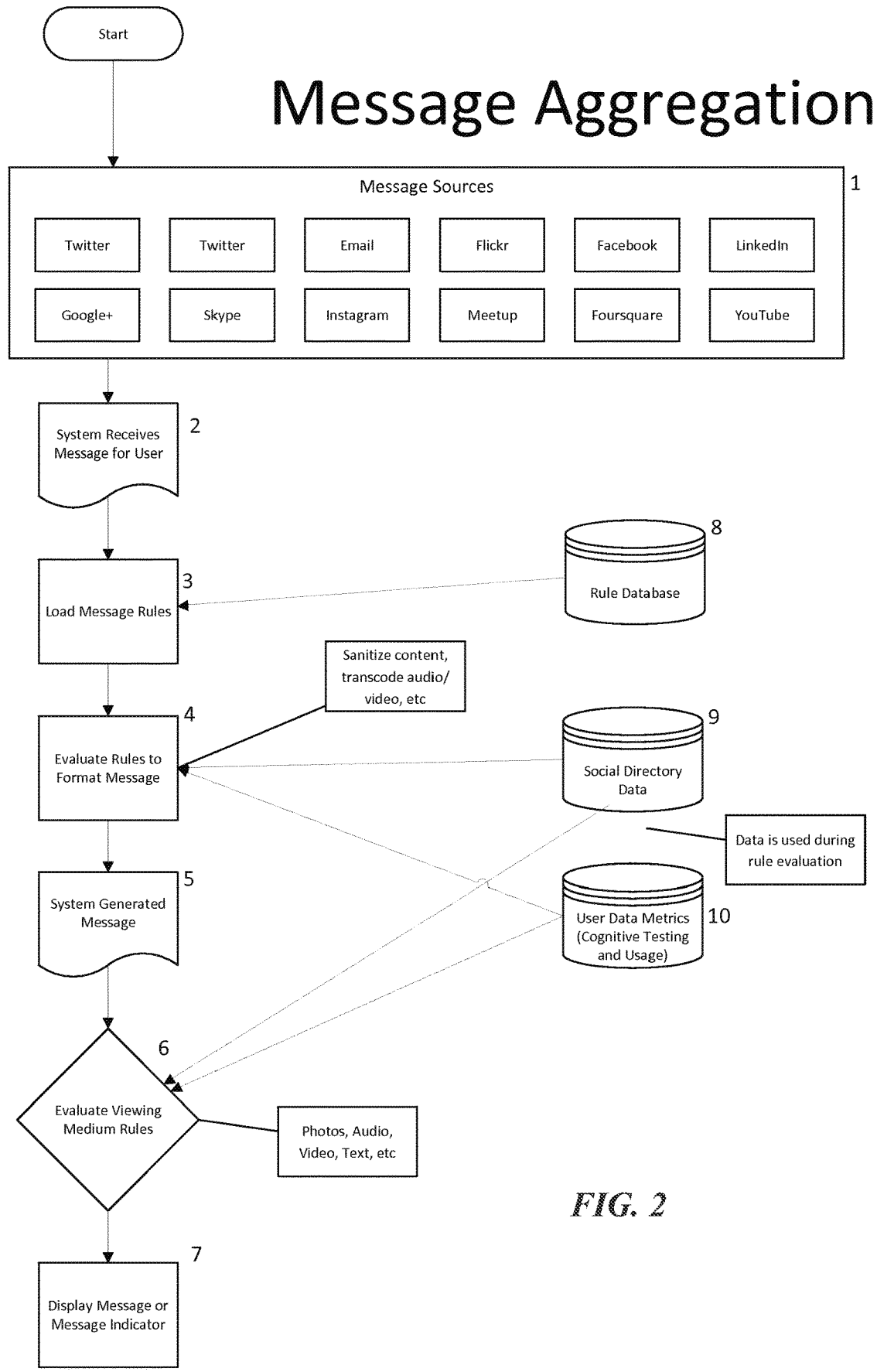
FIG. 2 is a flow chart illustrating message aggregation according to an embodiment of the current invention.

Referring to FIG. 2, message aggregation is a process, wherein the system receives messages from various sources and delivers them to the recipient in a unified interface and in a normalized format, regardless of the source (e.g., email, social networking, text message, etc.) of the message. The process utilizes rules for sanitizing and formatting the incoming messages, and for determining the viewing medium and presenting the incoming messages to the user/recipient.

The user benefits from this process because they can view messages from disparate message sources in a unified user interface. For low to medium functioning individuals, this presents a tremendous opportunity to "stay connected" with family, friends, news sources, etc. For high functioning individuals, a unified interface simplifies their messaging experience.

More specifically, still referring to FIG. 2, the system receives a message (2) from a message source (1). The system determines the user that is the destination of the message (2). The system loads a set of message rules (3) from a rule database (8). The rule database (8) contains dynamic rules that can be altered in real time by domain specialists or other authorized parties. Examples of domain specialists and authorized parties include, but are not limited to, clinical psychologists specializing in dementia, occupational therapists, specialists relating to impairments such as blindness and deafness, caretakers, etc.

This rule database (8) may include a variety of rules or guidelines as set by authorized parties. These rules may include, for example, primary and secondary modes/methods of communication, each having parameters (e.g., 140 characters or less for TWITTER) that should be met by the message being transmitted. The rules can further include guidelines that if the message does not meet the parameters of the primary mode/method of communication and/or cannot be formatted to meet the parameters, the message is sent via a secondary method of communication that has an alternate set of allowable message parameters to which the message can conform or be formatted to conform. Alternatively or in conjunction, messages containing text only may have a primary and/or secondary mode/method of communication, messages containing an image may have their own primary and/or secondary mode/method of communication, messages containing sound may have their own primary and/or secondary mode/method of communication, and messages containing a video may have their own primary and/or secondary mode/method of communication. In other words, the rules governing the primary/secondary modes/methods of communication may consider or be dependent on the content of the message when formatting/normalizing the message.

The system evaluates the rules from the rule database (8) in order to format the message (4) accordingly. The rules utilize message data, such as source system, destination user, and contents, for formatting the message (4). The rules may further utilize data from the user/recipient's social directory (9). The rules may further utilize the user/recipient's metric data (10), for example results of the user's cognitive testing/training, as previously described. As such, as cognitive abilities change, the rules can change, for example with regards to how simplistic or complex the message display can be.

Upon evaluating the preset rules (from the rule database (8)) and formatting the message received from the sender (5), the system generates a message (5) in the manner and format dictated by the rules (4) from the rule database (8). This message may be sanitized, reformatted, etc. Multimedia content may be transcoded to a universal format, such as .H264 for video or MP3 for audio. Similarly, images may be resized and encoded in a universal format, such as JPG.

The system generated message (5) is then evaluated against Viewing Medium Rules (6). The rules utilize message data, such as source system, destination user, and contents, for displaying the message (7). The rules may further utilize data from the user/recipient's social directory (9). The rules may further utilize the user/recipient's metric data (10), for example results of the user's cognitive testing/training, as previously described.

Evaluation of the Viewing Medium Rules (6) results in the system further formatting the message and/or displaying the message to the user (7). Examples of viewing mediums include, but are not limited to, a video player for YOUTUBE content, an image viewer for INSTAGRAM, FACEBOOK, and FLICKR images, and a "wall" or "timeline" format for blogs, forums, FACEBOOK, TWITTER, etc.

Example 3—Message Transmission/Distribution

Figure 3:
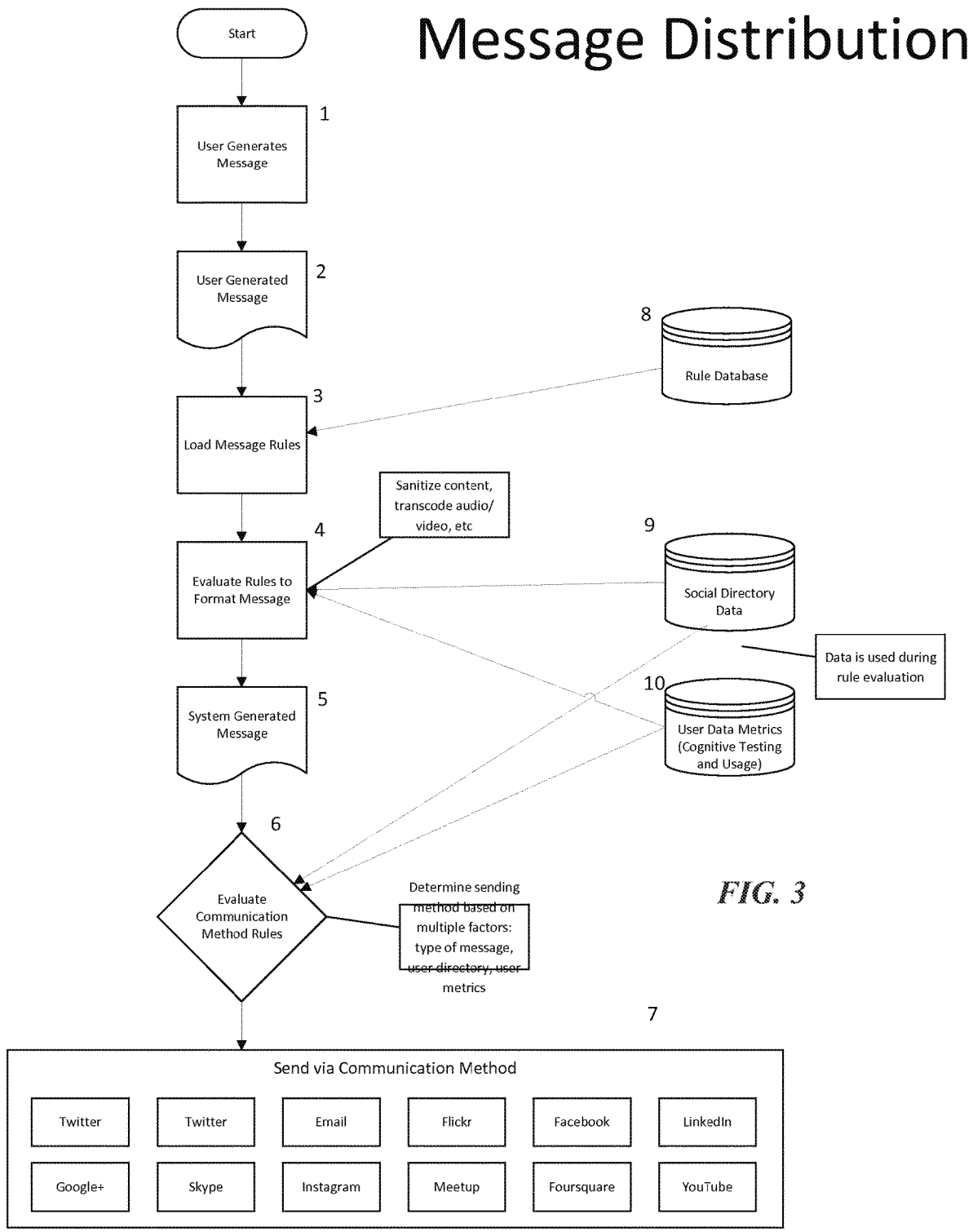
FIG. 3 is a flow chart illustrating message distribution according to an embodiment of the current invention.

Referring now to FIG. 3, message distribution is a process wherein the system transmits messages from a user in a unified interface to various sources (e.g., email, social networking, text message, etc.). The process utilizes rules for sanitizing and formatting the outgoing messages, and for determining the communication method and transmitting the outgoing messages to a recipient.

The user benefits from this process because they can generate messages in a unified, normalized user interface and transmit the message to disparate systems. For low-to-medium functioning individuals, in particular, the unified user interface presents an opportunity for the individual to communicate with family, friends, news sources, etc. more easily than having to utilize different systems/sources for different modes of communication (e.g., having to use FACEBOOK for FACEBOOK-related communications, TWITTER for TWITTER-related communications, and also INSTAGRAM for INSTAGRAM-related communications). For high-functioning individuals, a unified interface simplifies their messaging experience.

More specifically, still referring to FIG. 3, the user generates a new message (1), containing text, images, videos, and/or other multimedia formats. The system receives the user-generated message (2) and determines the destination. Examples of destinations include, but are not limited to, individuals and systems (e.g., TWITTER, INSTAGRAM, YOUTUBE, etc.)

Upon receiving the message (2), the system automatically loads a set of message rules (3) from a rule database (8). The rule database (8) contains dynamic rules that can be altered in real time by domain specialists or other authorized parties. Examples of domain specialists and authorized parties include, but are not limited to, clinical psychologists specializing in dementia, occupational therapists, specialists relating to impairments such as blindness and deafness, caretakers, etc.

This rule database (8) may include a variety of rules or guidelines as set by authorized parties. These rules may include, for example, primary and secondary modes/methods of communication, each having parameters (e.g., 140 characters or less for TWITTER) that should be met by the message being transmitted. The rules can further include guidelines that if the message does not meet the parameters of the primary mode/method of communication and/or cannot be formatted to meet the parameters, the message is sent via a secondary method of communication that has an alternate set of allowable message parameters to which the message can conform or be formatted to conform. Alternatively or in conjunction, messages containing text only may have a primary and/or secondary mode/method of communication, messages containing an image may have their own primary and/or secondary mode/method of communication, messages containing sound may have their own primary and/or secondary mode/method of communication, and messages containing a video may have their own primary and/or secondary mode/method of communication. In other words, the rules governing the source to which the message is being transmitted may consider or be dependent on the content of the message when formatting/normalizing the message.

The system evaluates the rules from the rule database (8) in order to format the message (4) accordingly. The rules utilize message data, such as source system, destination user, and contents, for formatting the message (4). The rules may further utilize data from the user/recipient's social directory (9). The rules may further utilize the user/recipient's metric data (10), for example results of the user's cognitive testing/training, as previously described. As such, as cognitive abilities change, the rules can change, for example with regards to how simplistic or complex the message display can be.

Upon evaluating the preset rules (from the rule database (8)) and formatting the message being transmitted (5), the system generates a message (5) in the manner and format dictated by the rules (4) from the rule database (8). This message may be sanitized, reformatted, etc. Multimedia content may be transcoded to a universal format, such as .H264 for video or MP3 for audio. Similarly, images may be resized and encoded in a universal format, such as JPG.

The system generated message (5) is then evaluated against Communication Method Rules (6). The rules utilize message data, such as source system, destination user, and contents, for transmitting the message (7). The rules may further utilize data from the user/recipient's social directory (9). The rules may further utilize the user/recipient's metric data (10), for example results of the user's cognitive testing/training, as previously described.

Evaluation of the Communication Method Rules (6) results in the system further formatting the message and/or transmitting the message to the recipient (7).

Evaluation of the Communication Method Rules (6) results in the system further formatting the message and/or transmitting the message to the recipient (7). Examples of communication methods include, but are not limited to, YOUTUBE for video content, INSTAGRAM, FACEBOOK, and FLICKR for image content, blogs, emails, forums, FACEBOOK, and TWITTER for text content, and FOURSQUARE for location content.

Hardware and Software Infrastructure Examples

The present invention may be embodied on various computing platforms that perform actions responsive to software-based instructions and most particularly on touch-screen portable devices. The following provides an antecedent basis for the information technology that may be utilized to enable the invention.

The computer readable medium described in the claims below may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any non-transitory, tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to, wireless, wire-line, optical fiber cable, radio frequency, etc., or any suitable combination of the foregoing. Computer program code for carrying out operations for aspects of the present invention may be written in any combination of one or more programming languages, including an object oriented programming language such as Java, C #, C++, Visual Basic or the like and conventional procedural programming languages, such as the "C" programming language or similar programming languages.

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

It should be noted that when referenced, an "end-user" is an operator of the software as opposed to a developer or author who modifies the underlying source code of the software. For security purposes, authentication means identifying the particular user while authorization defines what procedures and functions that user is permitted to execute.

Definition of Claim Terms

Cognitive ability: This term is used herein to refer to the mental (i.e., logic) acuity of a user, for example measured upon administration of one or more cognitive tests.

Cognitive test: This term is used herein to refer to any training method administered to a user and personalized based on the user's baseline cognitive ability, personal goal and real-time performance within training. Examples of training methods include, but are not limited to, free recall, graduated cuing, vanishing cues and spaced retrieval. However, each cognitive test has parameters that are modified and personalized to each user, and thus, each cognitive test is created via a unique combination of memory test techniques and performance parameters.

Computer-implemented instructions: This term is used herein to refer to a procedure or series of instructions for software carried out on a personal computer, tablet, smart phone or other electronic device.

Computer-readable data store: This term is used herein to refer to an integrated data or information repository. An example includes various types of databases. This data repository can be read by a computer or other electronic device, and access (i.e., the ability for a user to transmit instructions to a computer to read the data or information therein) is limited based on certain standards. For example, access may be limited by the cognitive abilities of a user.

Conform: This term is used herein to refer to being in accordance with a set of specifications or guidelines. For example, if a message must "conform" to a set of parameters contained within a particular medium of communication, the message must contain parameters that are in accordance or align with the set of parameters contained within the particular medium of communication.

Connection: This term is used herein to refer to a communications link between two individuals or contacts. The "connection" can be personal, professional, or non-personal. Examples of connections include, but are not limited to, family members, friends, caregivers, colleagues, resident and carrier (i.e., mail, packages, etc.), and other individuals who have any occasion to interact with each other.

Contacts: This term is used herein to refer to individuals in a user's social network or individuals that the user may have any occasion to communicate with or receive communications from, either digitally or in person.

Diverge: This term is used herein to refer to not being in accordance with a set of specifications or guidelines. For example, if a message "diverges" from a set of parameters contained within a particular medium of communication, the message contains parameters that are not in accordance or do not align with the set of parameters contained within the particular medium of communication.

External destination: This term is used herein to refer to an individual or system that is capable of receiving a communication, where the individual or system is positioned outside of the system of the current invention. For example, the external destination can be a family member of an individual suffering from dementia where the individual would use the current system, or can be a communication system used by the family member. If the external destination is a social media account of the family member, the family member can receive the communication from the individual where the communication is formatted and transmitted to the family member's social media account according to the parameters of the social media account. Further, when the family member responds to the communication through the social media account, the communication can be formatted and transmitted to the unified interface of the individual, according to the current invention.

External source: This term is used herein to refer to an individual or system that is capable of transmitting a message, where the individual or system is positioned outside the system of the current invention. For example, the external source can be a family member of an individual suffering from dementia where the individual would use the current system (i.e., internal destination), or can be a communication system used by the family member. If the external source is an email account of the family member, the family member can transmit a message to the individual, such that the message would be normalized for the individual receiving the message. Further, when the individual responds to the message through a unified interface according to the current invention, the message can be formatted and transmitted to the email account of the family member.

Format: This term is used herein to refer to the layout of a communication or message in a particular communication system, such that the format of the communication or message can be edited to fit different communication systems.

Individual: This term is used herein to refer to any end-user, operator or facilitator of the current invention. Examples include residents at assisted living facilities, sufferers of dementia, persons with suboptimal cognitive acuity, persons wishing to enhance or maintain cognitive ability, or persons in an end-user's social network, authorized parties or other individuals finding the current invention useful to achieve personal goals or objectives.

Internal destination: This term is used herein to refer to an individual or system that is capable of receiving a communication, where the individual or system is positioned within the system of the current invention. For example, the internal destination can be an individual with suboptimal cognitive ability, where the individual would use the current system. As an internal destination, this individual can receive communications from family, friends, caretakers, or others outside of the system (i.e., external sources). When the internal destination receives the communication, it has been formatted by the system to be displayed in an easy-to-read, unified interface.

Internal source: This term is used herein to refer to an individual or system that is capable of transmitting a message, where the individual or system is positioned within the system of the current invention. For example, the internal source can be an individual end-user with suboptimal cognitive ability living in an assisted living facility. As an internal source, this end-user can communicate with family, friends, caretakers, or others outside of the end-user's system (i.e., external destinations). When the end-user transmits a message to the external destination, the message is formatted and transmitted sent through a unified interface to the external destination (the external destination receives the message formatted according to the parameters of the external destination).

Message: This term is used herein to refer to any type of electronic communication, for example including, but not limited to, social information message, email, voice message, text message, video, or other electronic medium.

Parameters or message parameters: These terms are used herein to refer to conditions or characteristics required for a particular type of communication to be transmitted to a recipient. For example, a communication transmitted to a recipient through TWITTER may require 140 characters or less.

Primary method of communication: This term is used herein to refer to a primary medium of electronic communication preselected by an authorized party. Thus, when a user composes a message and transmits the message to the authorized party, the message is sent in the "primary method of communication." The message must meet the allowable message parameters of the primary method of communication. Otherwise, the message can be sent via a secondary method of communication.

Rule database: This term is used herein to refer to a module for receiving, storing, and outputting guidelines for formatting, transmitting, and displaying a communication or message.

Rules: This term is used herein to refer to guidelines for formatting, transmitting, and displaying a communication or message.

Secondary method of communication: This term is used herein to refer to a medium of electronic communication that is used when a user does not meet the allowable message parameters of a primary method of communication. For example, if a primary method of communication is TWITTER and a message is over 140 characters in length, the message may be transmitted via FACEBOOK, email or other medium.

Social directory: This term is used herein to refer to a group of individuals with which a user communicates, individuals who the user wishes to identify, individuals who communicate with the user, and/or individuals who are associated with the user. A user's social directory includes, but is not limited to, the user himself/herself, friends, family, educators, staff members implementing MRTS, assisted living facility staff, other residents in an assisted living facility and/or other authorized parties. A user's social network may have access to the user's directory, exercise portal, MRTS, etc.

It will thus be seen that the objects set forth above, and those made apparent from the foregoing disclosure, are efficiently attained. Since certain changes may be made in the above construction without departing from the scope of the invention, it is intended that all matters contained in the foregoing disclosure or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A method of treating dementia in a first individual by administering aggregated messages to the first individual comprising:

providing, to the first individual having a diagnosis of dementia, access to a computing device comprising one or more processors coupled to memory and a data store storing computer executable instructions which cause the computing device to perform steps comprising:

administering a baseline cognitive test and memory training to the first individual having a diagnosis of dementia to obtain baseline cognitive test results including a first measure of impairment of the first individual's mental acuity;

receiving a message from an external source intended for the first individual, said message including content in a format provided by said external source, wherein said content of said message includes video content and sound content;

determining an internal destination of said message, the internal destination associated with the first individual;

accessing a rule database and loading a first set of rules therefrom, said first set of rules being associated with the internal destination, the first set of rules considering the baseline cognitive test results including the first measure;

evaluating said first set of rules and automatically formatting said content of said message in order obtain formatted content that complies with said first set of rules, wherein automatically formatting said content includes normalizing the video content to a universal video format and normalizing the sound content to a universal sound format;

automatically generating a formatted message that includes the formatted content, wherein when the baseline test results indicate that the first individual consistently identifies the external source based on information obtained from the first individual's social directory, automatically generating the formatted message includes adding the information to the formatted message;

loading a second set of rules from the rule database, the second set of rules associated with a visual display of said formatted message, the second set of rules being associated with the baseline test results including the measure of impairment;

displaying said formatted message on a display device associated with said internal destination in accordance with said second set of rules; and monitoring the first individual's interaction with the formatted message while displayed on the display device to determine a length of time it takes the first individual to read the formatted message, wherein the second set of rules includes a rule for displaying the formatted message in accordance with the length of time.

2. The method as in 1, the steps further comprising:

said first set of rules including a primary method of communication for said internal destination, wherein said primary method of communication is associated with a first parameter associated with the content of the message; and said instructions further comprising:
  determining whether said content meets said first parameter,
  when the message meets the first parameter, receiving said message via said primary method of communication, and
  when the message fails to meet the first parameter, receiving said message via a secondary method of communication.

3. The method as in 1, wherein the first set of rules contains at least one rule associated with at least one of:
  a source of the message;
  a length of the message;
  the message contains an image;
  or
  the message conforms to a parameter.

4. The method as in 1, wherein said first or second set of rules incorporates a rule associated with said external source of said message.

5. The method as in claim 2, wherein the primary method of communication is via a blog, an email, a forum, a text message, or a social media channel.

* * * * *